US008901433B2

(12) United States Patent
Devadoss

(10) Patent No.: US 8,901,433 B2
(45) Date of Patent: Dec. 2, 2014

(54) INDIVIDUALLY ADDRESSABLE BAND ELECTRODE ARRAYS AND METHODS TO PREPARE THE SAME

(75) Inventor: Anando Devadoss, Irvine, CA (US)

(73) Assignees: Hitachi Chemical Co., Ltd., Tokyo (JP); Hitachi Chemical Research Center, Inc., Irvine, CA (US)

( * ) Notice: Subject to any disclaimer, the term of this patent is extended or adjusted under 35 U.S.C. 154(b) by 152 days.

(21) Appl. No.: 13/820,994

(22) PCT Filed: Sep. 12, 2011

(86) PCT No.: PCT/US2011/001568
§ 371 (c)(1),
(2), (4) Date: Mar. 8, 2013

(87) PCT Pub. No.: WO2012/033539
PCT Pub. Date: Mar. 15, 2012

(65) Prior Publication Data
US 2013/0168135 A1    Jul. 4, 2013

Related U.S. Application Data

(60) Provisional application No. 61/381,714, filed on Sep. 10, 2010.

(51) Int. Cl.
| H05K 1/11 | (2006.01) |
| H05K 3/10 | (2006.01) |
| G01N 27/27 | (2006.01) |
| H01R 43/16 | (2006.01) |

(52) U.S. Cl.
CPC .................. *H05K 1/11* (2013.01); *G01N 27/27* (2013.01); *H01R 43/16* (2013.01)
USPC .............................. 174/261; 174/255; 29/846

(58) Field of Classification Search
USPC ..................... 174/255–261, 262–266; 29/846; 361/792–795
See application file for complete search history.

(56) References Cited

U.S. PATENT DOCUMENTS

| 6,110,354 A | 8/2000 | Saban et al. |
| 6,350,431 B1 | 2/2002 | Snow et al. |

(Continued)

FOREIGN PATENT DOCUMENTS

| WO | 2005/121762 A1 | 12/2005 |
| WO | 2007/086268 A1 | 8/2007 |

OTHER PUBLICATIONS

English translation of Office Action dated May 8, 2014 corresponding to Japanese Patent Application No. 2013-501255, 2 pages.

(Continued)

*Primary Examiner* — Jeremy C Norris
(74) *Attorney, Agent, or Firm* — Dentons US LLP

(57) ABSTRACT

Band electrode arrays, methods of manufacturing, and a method of using are disclosed. The arrays have individually addressable band electrodes such that diffusion layers of the band electrodes overlap. An exemplary method of manufacturing may comprise: a first insulating layer is disposed on a substrate; a first band electrode is disposed on the first insulating layer; a second insulating layer is disposed on the first insulating layer and completely covers the first band electrode; a second band electrode is disposed on the second insulating layer; a third insulating layer is disposed on the second insulating layer and completely covers the second band electrode; the first and second band electrodes are electrically insulated from each other and individually addressable; cross-sectional surfaces of the first and second band electrodes are exposed on the test surface; and these exposed cross-sectional surfaces substantially overlap each other in a direction perpendicular to the substrate.

23 Claims, 6 Drawing Sheets

(56) References Cited

U.S. PATENT DOCUMENTS

| | | | |
|---|---|---|---|
| 6,424,993 | B1 | 7/2002 | Weber |
| 6,921,469 | B2 | 7/2005 | Larsen |
| 7,144,486 | B1 | 12/2006 | Fritsch et al. |
| 2002/0058279 | A1 | 5/2002 | Fritsch et al. |
| 2004/0248381 | A1 | 12/2004 | Myrick |
| 2006/0267480 | A1 | 11/2006 | Kusunoki et al. |
| 2007/0017571 | A1 | 1/2007 | Gaudiana et al. |
| 2008/0246387 | A1 | 10/2008 | Kusunoki et al. |
| 2009/0221762 | A1 | 9/2009 | Therien et al. |
| 2009/0302873 | A1 | 12/2009 | Haggett et al. |
| 2010/0090260 | A1 | 4/2010 | Fredrick et al. |

OTHER PUBLICATIONS

Kovach et al., "Faradaic Electrochemistry at Microcylinder, Band and Tubular Band Electrodes", J. Electroanal. Chem., 1985, pp. 285-295, vol. 185.

Wehmeyer et al., "Electroanalytical Properties of Band Electrodes of Submicrometer Width" Anal. Chem., 1985, pp. 1913-1916, vol. 57.

Welford et al., "Laminated Microelectrodes: A Simple Approach to the Construction of Inexpensive Microelectrodes with a Variety of Geometries", Anal. Chem., 2001, pp. 6088-6609.

Dressman et al., "Carbon fiber microelectrodes with multiple sensing elements for in vivo voltammetry," Journal of Neuroscience Methods, 2002, pp. 75-81, vol. 119.

Droge et al., "Multielectrode Analysis of Coordinated, Multisite, Rhythmic Bursting in Cultured CNS Monolayer Networks," The Journal of Neuroscience, 1986, pp. 1583-1592, vol. 6, No. 6.

Gavin et al., "Continous Seperations with Microfabricated Electrophoresis—Electrochemical Array Detection," J. Am. Chem. Soc., 1996, pp. 8932-8936, vol. 118.

Hafez et al., "Electrochemical imaging of fusion pore openings by electrochemical detector arrays," PNAS, 2005, pp. 13879-13884, vol. 102, No. 39.

Light et al., "Time and Spatial Dependence of the Concentration of Less Than 105 Microelectrode-Generated Molecules," Science, 1989, pp. 1176-1178, vol. 243.

Maher et al., "The neurochip: a new multielectrode device for stimulation and recording from cultured neurons," Journal of Neuroscience Methods, 1999, pp. 45-56, vol. 87.

Morris et al., "Electrochemistry at Pt Band Electrodes of Width Approaching Molecular Dimensions. Breakdown of Transport Equation at Very Small Electrode," J. Phys. Chem., 1987, pp. 3559-3564, vol. 91.

Nagale et al., "Individually Addressable, Submicrometer Band Electrode Arrays. 1. Fabrication from Multilayered Materials," Anal. Chem., 1998, pp. 2902-2907, vol. 70.

Sreenivas et al., "Fabrication and Characterization of Sputtered-Carbon Microelectrode Arrays," Anal. Chem., 1996, pp. 1858-1864, vol. 68.

Stett et al., "Biological application of microelectrode arrays in drug discovery and basic research," Anal. Bioanal. Chem., 2003, pp. 486-495, vol. 377.

Suzuki et al., "Stepwise pattern modification of neuronal network in photo-thermally-etched agarose architecture on multi-electrode array chip for individual-cell-based electrophysiological measurement," Lab Chip, 2005, pp. 241-247, vol. 5.

Yeung et al., "Drug profiling using planar microelectrode arrays," Anal. Bioanal. Chem., 2007, pp. 2673-2680, vol. 387.

Zhang et al., "Spatially and Temporally Resolved Single-Cell Exocytosis Utilizing Individually Addressable Carbon Microelectrode Arrays," Anal. Chem., 2008, pp. 1394-1400, vol. 80.

International Search Report and Written Opinion issued on Dec. 30, 2011, by the US Patent and Trademark Office as the International Searching Authority in International Patent Application No. PCT/US2011/001568.

INDIVIDUALLY ADDRESSABLE BAND ELECTRODE ARRAYS AND METHODS TO PREPARE THE SAME

FIELD

The present invention relates to arrangements, devices and methods associated with band electrodes, including electrochemical sensors.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Analytical techniques can provide powerful tools for testing of a wide variety of samples, such as, drinking water, waste water, and biological fluids such as blood and urine. One category of such techniques rely upon electrochemical reactions of analytes. A typical electrochemical cell shown in FIG. 1 comprises a container 110, a working electrode 120, a counter electrode 130, and a reference electrode 140. The three electrodes are immersed in an analyte solution 150 in the container 110. The reference electrode 140 provides a fixed voltage relative to the analyte solution 150. During use, a voltage signal is applied to the working electrode 120 relative to the reference electrode 140; electrical current flows between the working electrode 120 and the counter electrode 130; and no electrical current flows through the reference electrode 140. A common electrochemical testing technique is cyclic voltammetry (CV), in which voltage on the working electrode 120 is ramped linearly versus time and a peak appears in the current between the working electrode 120 and the counter electrode 130 when any analyte is reduced or oxidized. The current is often limited by diffusion of chemical species to the surfaces of the working electrode 120 and the counter electrode 130. In conventional electrochemical cells, the physical distance between the electrodes is on the order of centimeters. Diffusion of the chemical species over such distance limits the temporal and quantitative sensitivities of these conventional electrochemical cells.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

SUMMARY

The present invention may address one or more of the problems and deficiencies of the prior art discussed above. However, it is contemplated that the invention may prove useful in addressing other problems and deficiencies, or provide benefits and advantages, in a number of technical areas. Therefore the claimed invention should not necessarily be construed as limited to addressing any of the particular problems or deficiencies discussed herein.

According to certain aspects, described herein is a band electrode array comprising: a substrate, a first insulating layer, a second insulating layer, a third insulating later, a first band electrode, a second band electrode and a test surface, wherein: the first insulating layer is disposed on the substrate; the first band electrode is disposed on the first insulating layer; the second insulating layer is disposed on the first insulating layer and completely covers the first band electrode; the second band electrode is disposed on the second insulating layer; the third insulating layer is disposed on the second insulating layer and completely covers the second band electrode; the first and second band electrodes are electrically insulated from each other and individually addressable; cross-sectional surfaces of the first and second band electrodes are exposed on the test surface; and these exposed cross-sectional surfaces substantially overlap each other in a direction perpendicular to the substrate.

According to another aspect, the present invention provides a band electrode array comprising: a substrate; a first insulating layer disposed on the substrate; a first band electrode disposed on the first insulating layer; wherein the first band electrode has a thickness of about 1 nm-about 5000 nm and an exposed cross-sectional surface having a width of about 1 μm-about 1 cm; a second insulating layer disposed on the first insulating layer and completely covering the first band electrode; wherein the second insulating layer has a thickness of about 100 nm-about 500 μm; a second band electrode disposed on the second insulating layer; wherein the thickness of the second band electrode is about 1 nm-about 5000 nm and width of the exposed cross-sectional surface of the second band electrode is about 1 μm-about 1 cm; a third insulating layer is disposed on the second insulating layer and completely covering the second band electrode; wherein the first and second band electrodes are electrically insulated from each other and individually addressable; cross-sectional surfaces of the first and second band electrodes are exposed on the test surface and coextensive with the test surface; and the exposed cross-sectional surfaces substantially overlap each other in a direction perpendicular to the substrate.

DETAILED DESCRIPTION

Unless otherwise defined herein or below in the remainder of the specification, all technical and scientific terms used herein have meanings commonly understood by those of ordinary skill in the art to which the present invention belongs.

Before describing the present invention in detail, it is to be understood that the terminology used in the specification is for the purpose of describing particular embodiments, and is not necessarily intended to be limiting. As used in this specification and the appended claims, the singular forms "a", "an" and "the" do not preclude plural referents, unless the context clearly dictates otherwise.

Figure 1:
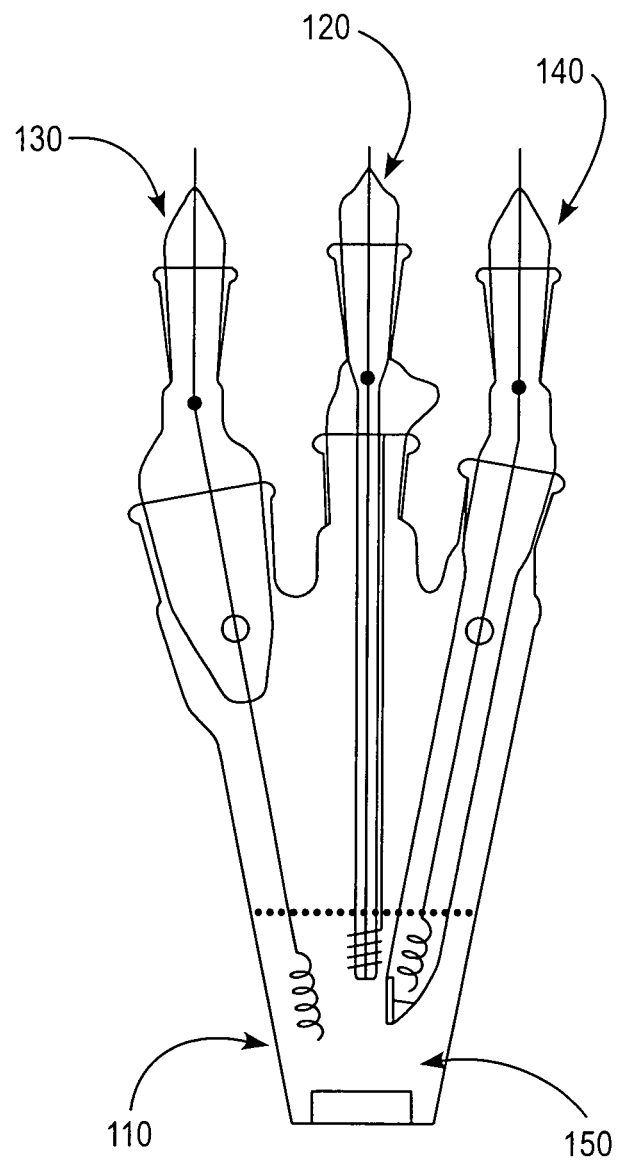
FIG. 1 shows a conventional electrochemical cell with a working electrode, a reference electrode and a counter electrode.
Figure 2:
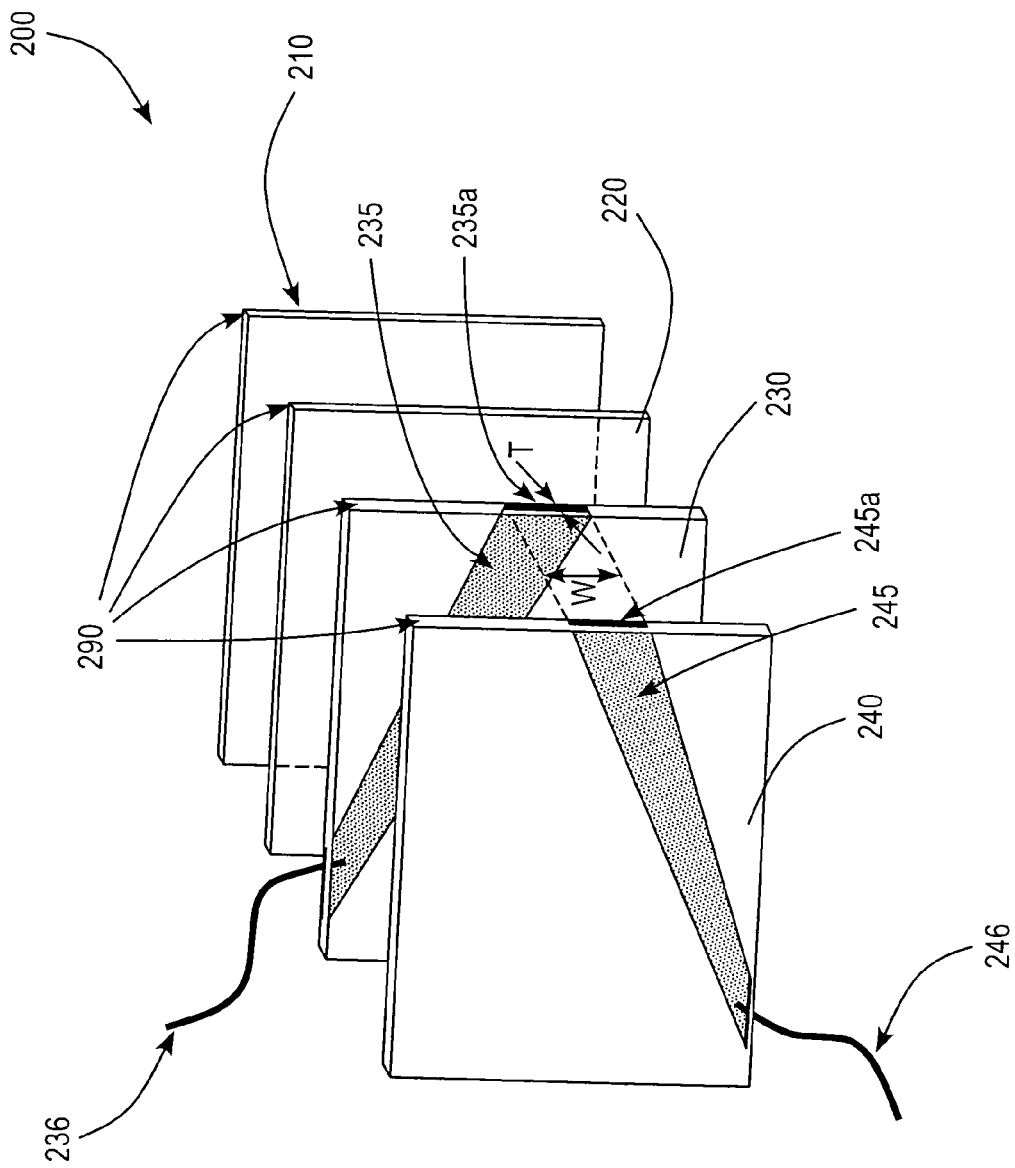
FIG. 2 shows an exploded view of a band electrode array according to an embodiment.

FIG. 2 shows an exploded view of a band electrode array (BEA) 200 according an embodiment. The BEA 200 may comprise a substrate 210, a first insulating layer 220, a second insulating layer 230, a third insulating layer 240, a first band electrode 235, and a second band electrode 245. The first insulating layer 220 can be disposed on the substrate 210. The first band electrode 235 can be disposed on the first insulating layer 220. The second insulating layer 230 can be disposed on the first insulating layer 220 and may completely cover the first band electrode 235. The second band electrode 245 can be disposed on the second insulating layer 230. The third insulating layer 240 can be disposed on the second insulating layer 230 and may completely cover the second band electrode 245. The substrate 210 can be made of any suitable material such as silicon, glass, plastic, rubber, silicone and/or combination thereof. The insulating layers 220, 230 and 240 can be made of any suitable electrically insulating material such as epoxy, polymer, oxide, nitride, carbide, plastic, silicone, rubber and/or combination thereof. The insulating layers 220, 230 and 240 can be applied by any suitable method such as spin coating, physical vapor deposition, chemical vapor deposition, drop casting and printing. The band electrodes 235 and 245 can be made of any suitable conductor such as gold, silver, copper, platinum, palladium, carbon, conductive polymer, metal alloy, and/or combination or mixture thereof. The band electrodes 235 and 245 can be deposited by any suitable method such as spin coating, physical vapor deposition, chemical vapor deposition, drop casting and printing. Cross-sectional surfaces 235a and 245a of the band electrodes 235 and 245 are exposed on at least one side surface 290 of the BEA (this side surface referred to as the "test surface" hereafter), and these cross-sectional surfaces 235a and 245a may substantially overlap (e.g., at least 50% of their widths, at least 70% of their widths, or at least 90% of their widths) each other in a direction perpendicular to the substrate 210. Exposed cross-sectional surfaces 235a and 245a of the band electrodes 235 and 245 can be coextensive with test surface(s) 290. The exposed cross-sectional surfaces 235a and 245a of the band electrodes 235 and 245 can be functionalized with the same of different chemical species. For example, in case of gold electrodes, the test faces can be selectively cleaned electrochemically to deposit alkane thiols with different end groups on each electrode. In case of carbon electrodes, each individual electrode can be selectively modified by electrochemical reduction of aromatic diazonium ions with different end groups or electrochemical oxidation of aliphatic amines with different end groups. Alternatively, the exposed surfaces of the band electrodes can be functionalized by aromatic amines with different end groups, aliphatic or aromatic alcohols with different end groups, aliphatic and/or aromatic carboxylic compounds with different end groups, or dihydroxy bezaldehydes with different end groups.

The band electrodes 235 and 245 may have any suitable thickness (T), such as a thickness of about 1 nm to about 5000 nm, about 5 nm to about 2000 nm, or about 90 nm to about 110 nm. Either or both band electrodes 235, 245 can be formed from a single layer, or can be formed by a plurality of layers. The above thicknesses represent the total thickness values. The cross-sectional surfaces 235a and 245a of the band electrodes 235 and 245 on the test surface(s) 290 may have any suitable width (W), such as a width of about 1 μm to about 1 cm, about 1 μm to about 5000 μm, about 10 μm to about 1000 μm, or about 100 μm to about 500 μm. It should be noted that the band electrodes 235 and 245 may have the same thickness, or their thicknesses may differ. Similarly, the width of the cross-sectional surfaces 235a and 245a may be the same, or they may differ.

Figure 3:
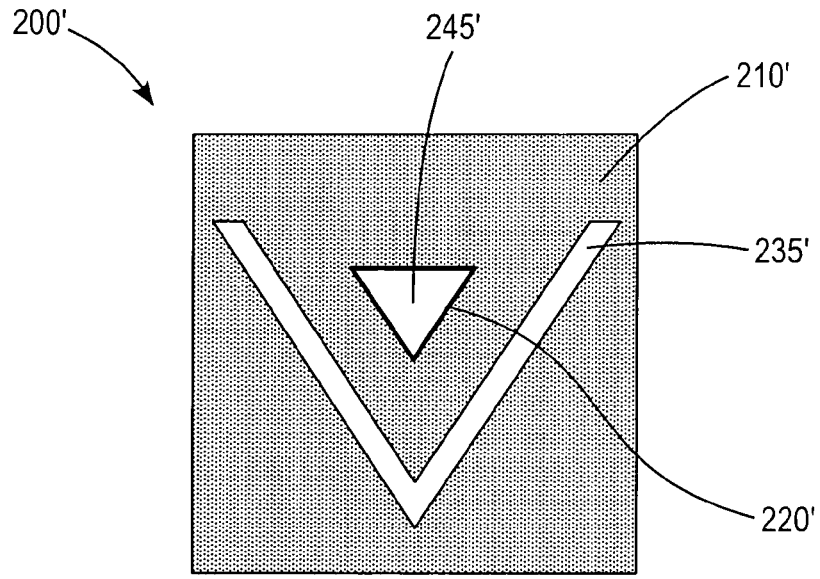
FIG. 3 is a top view of a band electrode array according to an additional optional embodiment.

The band electrodes 235 and 245 can be separated by the second insulating layer 230, whose thickness can be sufficient to withstand any electrical potential difference between the band electrodes 235 and 245 (e.g., up to 10 V) during use of the BEA 200, such as a thickness of about 100 nm to about 500 μm, about 100 nm to about 5 μm, or about 1 μm to about 2 μm. The band electrodes 235 and 245 can be electrically insulated from each other, are individually addressable and can be respectively connected to electrical leads 236 and 246 (by a suitable method such as conductive adhesive, soldering, wire bonding) for applying and/or sensing electrical signals on the band electrodes 235 and 245. The substrate and/or band electrodes 235 and 245 can have any suitable shape or geometry when viewed from a direction perpendicular to the substrate 210. For example, as illustrated in FIG. 3, an alternative BEA 200', a first band electrode 235' can be formed on the substrate 210' and have a substantially triangular or wedge shape. The second band electrode 245' can also be provided with a substantially triangular or wedge shape, and be separated electrically from the first band electrode 235' by an insulating layer 220'.

Figure 4:
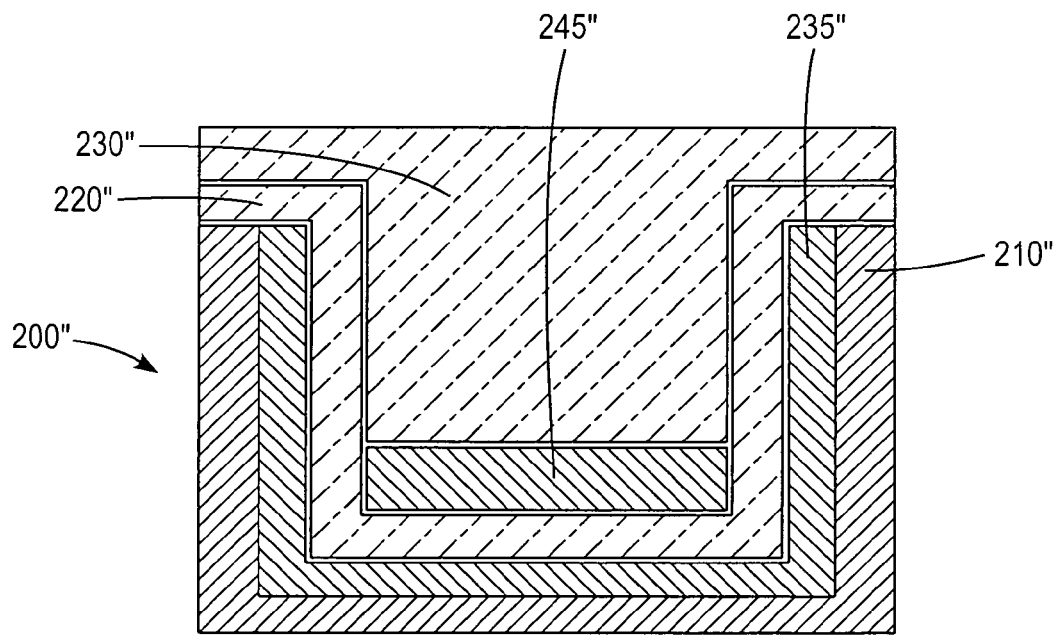
FIG. 4 is a cross-sectional view of a band electrode array formed according to another optional embodiment.

Moreover, the BEA 200 and its associated substrate, band electrodes and insulating layers need not be planar. Thus, the BEA of the present invention can be curvilinear or in the form of a rectilinear polygon, to give a few examples. An optional alternative BEA 200" of the present invention is illustrated in FIG. 4. As illustrated therein, the substrate 210" is in the form of a rectilinear polygon, such as generally U-shaped. A first band electrode 235" can be provided thereon, followed by a first insulating layer 220", and a second band electrode 245". A second insulating layer 230" may also be provided. As seen in FIG. 4, the first band electrode 235" can surround the second band electrode 245" by, for example, shape and/or thickness of the insulating layer 220". As with the previously described embodiments and optional features of the BEA, the substrate, band electrodes, and/or insulating layer(s) can have any of the properties, and/or be constructed according to any of the principles, as described herein.

Figure 5:
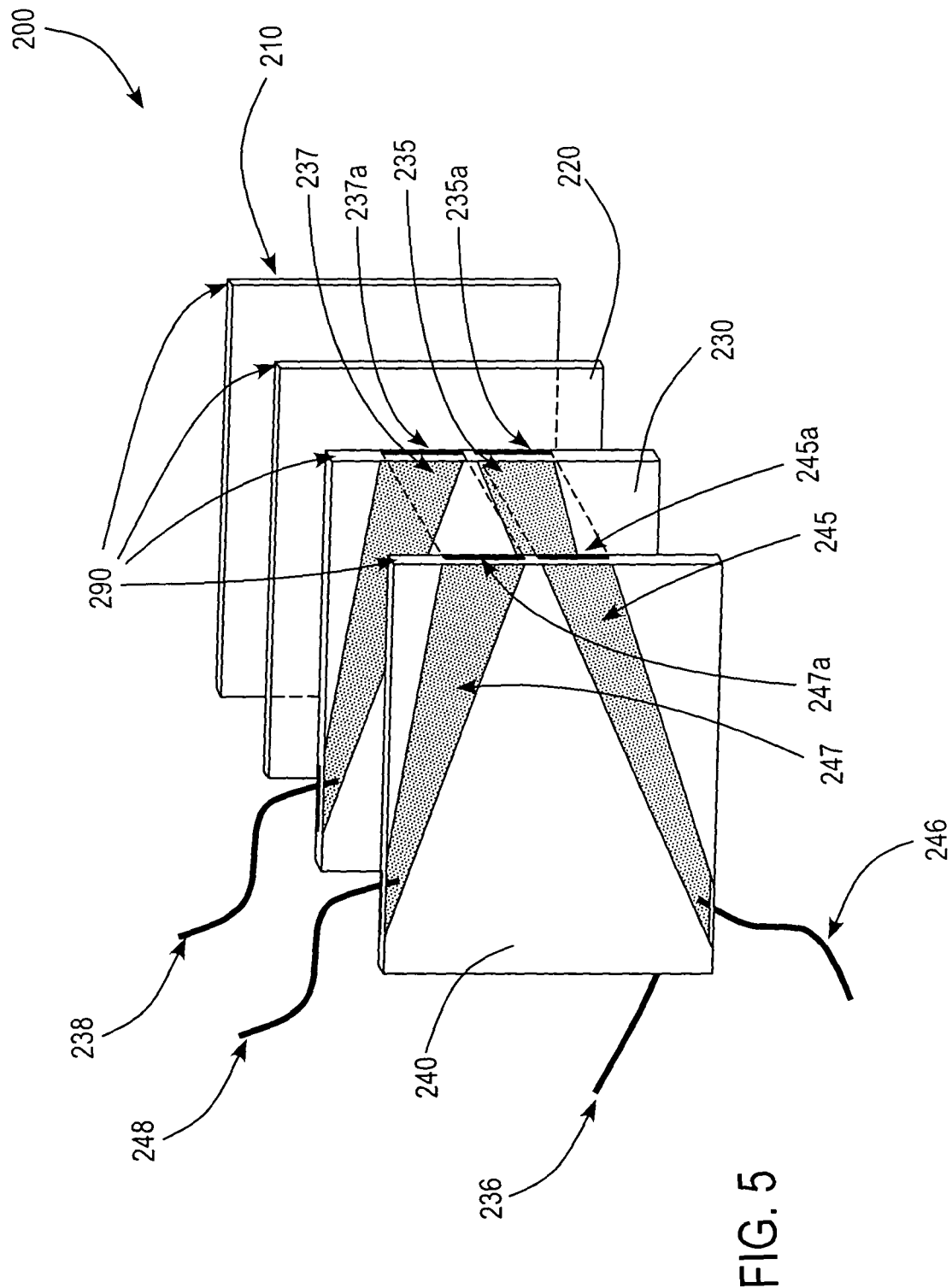
FIG. 5 shows an exploded view of a band electrode array according to a further embodiment.

As illustrated in FIG. 5, the BEA 200 can optionally comprise more than one band electrode disposed on the first insulating layer 220. All band electrodes disposed on the first insulating layer 220 may be completely covered by the second insulating layer 230. The BEA 200 can optionally comprise more than one band electrode disposed on the second insulating layer 230. All band electrodes disposed on the second insulating layer 230 may be completely covered by the third insulating layer 240. FIG. 5 shows two band electrodes 235 and 237 disposed on the first insulating layer 220 and two band electrodes 245 and 247 disposed on the second insulating layer 230. The band electrode 237 has an exposed cross-sectional surface 237a and can be connected to a lead 238. The band electrode 247 has an exposed cross-sectional surface 247a and can be connected to a lead 248. All band electrodes in the BEA can be electrically insulated from each other and individually addressable. Any or all of the band electrodes can have dimensions and be constructed as described in connection with the description of the first and second band electrodes. In addition, the BEA can have any suitable number of band electrodes and/or insulating layers.

Figure 6:
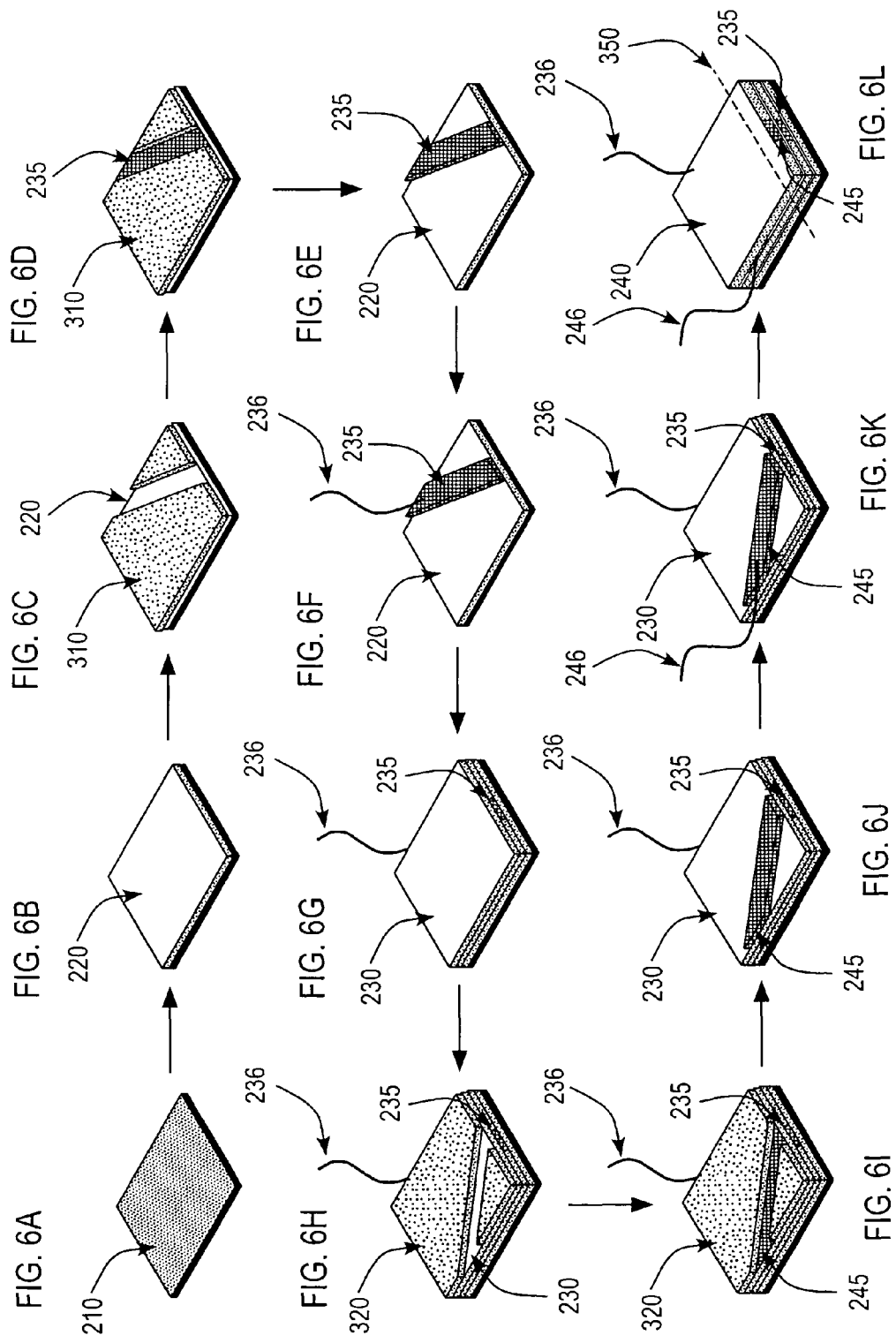
FIGS. 6A-6L shows various steps of a method of manufacturing the band electrode array of FIG. 2 according to an embodiment.

FIGS. 6A-6L show steps of an exemplary method of manufacturing the BEA 200 shown in FIG. 2, according to an embodiment. The method may comprise (i) depositing the first insulating layer 220 onto the substrate 210 (FIG. 6B), (ii) placing a first shadow mask 310 (such as a Ni or stainless steel stencil available from Photo Etch Technology, Lowell, Mass., USA) on the first insulating layer 220 (FIG. 6C), (iii) forming the first band electrode 235 in an opening of the first shadow mask 310 by depositing a conductive film over the first shadow mask 310 (FIG. 6D), (iv) removing the first shadow mask 310 (FIG. 6E), (v) optionally electrically connecting the lead 236 to the first band electrode 235 (FIG. 6F), (vi) depositing the second insulating layer 230 such that the first band electrode 235 is completely covered by the second insulating layer 230 (FIG. 6G), (vii) placing a second shadow mask 320 (such as a Ni or stainless steel stencil available from Photo Etch Technology, Lowell, Mass., USA) on the second insulating layer 230 (FIG. 6H), (viii) forming the second band electrode 245 in an opening of the second shadow mask 320 by depositing a conductive film over the second shadow mask 320 (FIG. 6I), (ix) removing the second shadow mask 320 (FIG. 6J), (x) optionally electrically connecting the lead 246 to the second band electrode 245 (FIG. 6K), (xi) depositing the third insulating layer 240 such that the second band electrode 245 is completely covered by the third insulating layer 240 (FIG. 6L), and (xii) cleaving or cutting a side surface 350 of the BEA to form the test surface 290 such that cross-sectional surfaces 235a and 245a of the band electrodes 235 and 245 are exposed thereon and substantially overlap each other in a direction perpendicular to the substrate 210 (FIG. 6L). The test surface 290 can be polished by a suitable method such as chemical mechanical polishing (CMP). This method of manufacturing BEAs, with regard to the dimensions of the electrodes exposed on the test surface, does not use any lithography techniques such as photolithography and e-beam lithography.

The method of manufacture above can further comprise functionalizing the exposed cross-sectional surface 235a of the first band electrode 235 with a first chemical species, and/or functionalizing the exposed cross-sectional surface 245a of the second band electrode 245 with a second chemical species. A method of functionalizing one or more of the band electrodes may comprise immersing the test surface 290 of the BEA 200, a reference electrode (e.g., a saturated calomel electrode, a Ag/AgCl reference electrode) and a counter electrode (e.g., a platinum wire or mesh) in an electrolyte in an electrochemical cell, applying a voltage on the one or more band electrode(s) relative to the reference electrode such that a desired electrochemical reaction is induced on the exposed cross-sectional surface(s) of the one or more band electrode(s) and a desired chemical species is deposited thereon, optionally applying another voltage at the same time to the other band electrode(s) relative to the reference electrode such that no electrical current flows through the other band electrode(s).

The BEA 200 described above can be used in an electrochemical cell as multiple working electrodes. For example, the test surface 290 of the BEA 200, a reference electrode (e.g., a saturated calomel electrode, a Ag/AgCl electrode) and a counter electrode (e.g., a platinum wire or mesh) are immersed in an analyte solution. A first voltage signal is applied to the first band electrode 235 such that an electrochemical reaction is induced on the exposed cross-sectional surface 235a of the first band electrode 235 and a reaction product is generated in the vicinity thereof. A second voltage signal is applied to the second band electrode 245 such that the reaction product undergoes another electrochemical reaction on the exposed cross-sectional surface 245a of the second band electrode 245 and a resultant electrical current flows through the second band electrode 245. This electrical current can be detected and analyzed to determine characteristics of the electrochemical reaction on the first band electrode 235 and properties of the reaction product such as the chemical nature, diffusion behaviors and concentration. The first voltage signal and the second voltage signal can be constant DC voltages or voltages changing with time (e.g., triangular voltage signals, pulse voltage signals, sawtooth voltage signals, staircase signals, etc.). Due to the proximity of the first and second band electrodes 235 and 245, the reaction product from the first band electrode 235 does not have to diffuse far before being detected by the second band electrode 245. As a result, the BEA 200 described herein has enhanced quantitative and temporal sensitivities compared to conventional BEAs.

The BEA 200 described above can also be used as both a working electrode and a counter electrode. For example, in a CV measurement, a sweeping voltage signal can be applied to the first band electrode 235 as the working electrode, relative to a reference electrode and the second band electrode 245 can be electrically grounded as the counter electrode.

The BEA 200 described here is not limited to only two band electrodes. This BEA can have multiple layers and each layer can have more than one band electrode. Separation between the layers is determined by the thickness of the insulating layers and thus can be very small and easily controlled, such that diffusion layers of adjacent band electrodes preferably overlap. The diffusion layer (boundary layer) of a band electrode is a volume of analyte solution between where the analyte is at bulk concentration and where the analyte concentration approaches zero (i.e. an interface between the analyte solution and the band electrode).

The delayed activation or a deferral of sensing functionality of a band electrode in a BEA having multiple that electrodes is also attainable according to the principles of the present invention. For example, initially, an electrochemical signal is applied to a first band electrode, which senses the signal applied thereto. After used in this manner over a period of time, the first band electrode may lose its ability to detect. Upon the loss of such ability by the first band electrode, an electrochemical signal could then be applied to a second band electrode, that was optionally previously inactive or nonfunctional, and the tension continued utilizing second band electrode. This delayed activation order for all of sensing functionality could then be repeated multiple times for additional band electrodes which may be present in the BEA. Therefore, according to this arrangement and mode of functionality, the lifetime of an arrangement which relies upon a single sensor or band electrode can be greatly lengthened, and reliability considerably improved.

Further principles and aspects of the present invention can be illustrated by reference to the following exemplary, and optional, embodiment of the present invention.

EXAMPLE

Figure 7:
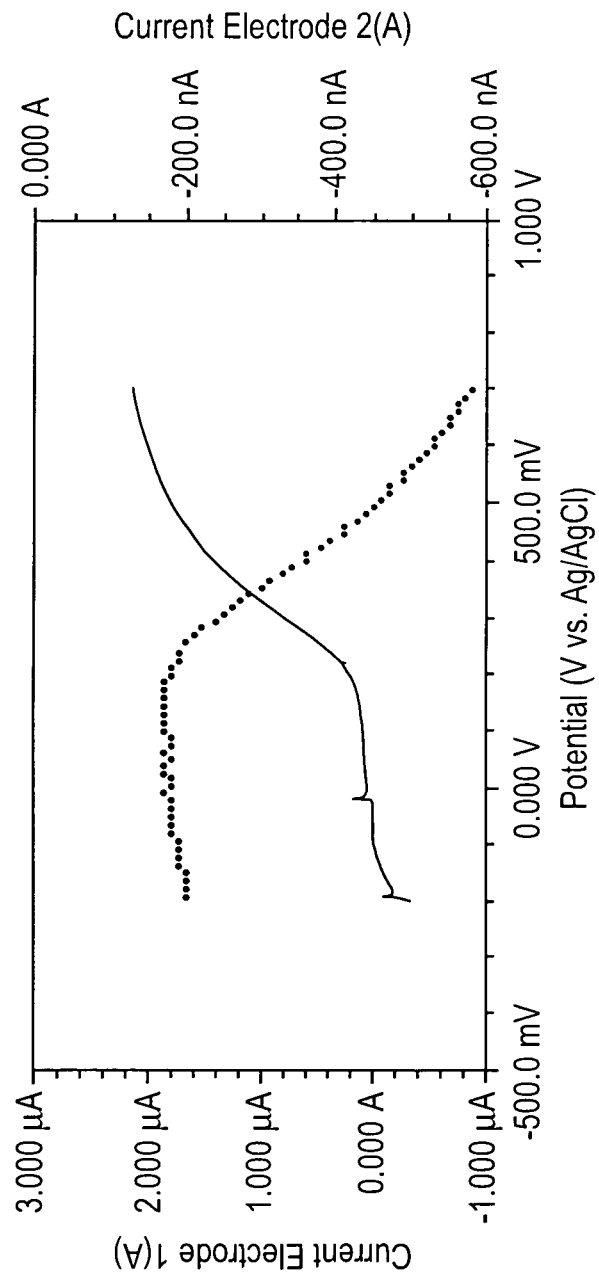
FIG. 7 is a plot of voltage vs. current for an exemplary embodiment of an electrochemical sensor.

A band electrode array was constructed including two carbon electrodes of 300 nm thickness and 0.7 cm width separated by a 70 μm silicone insulating layer. The band electrode array and a reference electrode (Ag/AgCl reference electrode model "CHI111" commercially available from CH Instruments, Inc., Austin, Tex.) were introduced into an aqueous solution containing 10 mM potassium ferrocyanide and 0.1 M potassium chloride supporting electrolyte. A variable voltage signal is applied to the first carbon electrode (C1). A constant voltage of −0.1V is applied to the second carbon electrode (C2). The solid line depicted in FIG. 7 is the voltammogram obtained from the first carbon electrode C1. As C1 generates oxidized ferrocyanide at potentials above 0.3 V, current at the second carbon electrode (C2) is measured. As illustrated by the dotted line in FIG. 7, the current at the second carbon electrode (C2) due to detection of the oxidized ferrocyanide increases (refer in particular to the right-hand X-axis of FIG. 7). Thus, diffusion of the chemical species from the above-described reaction is detectable by the band electrode array.

While a BEA, a method of manufacturing and a method of use of the BEA have been described in detail with reference to specific embodiments thereof, it will be apparent to those skilled in the art that various changes and modifications can be made, and equivalents employed, without departing from the scope of the appended claims.

Construction of three electrode system, where a working electrode, counter electrode and reference electrodes are embedded in one system. Similarly a four electrode system, where one electrode generates a species that is detected at another electrode, another electrode as counter electrode and another as reference electrode is also contemplated.

All numbers expressing quantities of ingredients, constituents, reaction conditions, and so forth used in the specification are to be understood as being modified in all instances by the term "about." In addition, all numbers and numerical ranges disclosed herein is also intended to encompass the literal numerical value or range as if it were unmodified by the term "about." Also, all numerical ranges disclosed herein encompass their end points or limits. Notwithstanding that the numerical ranges and parameters set forth, the broad scope of the subject matter presented herein are approximations, the numerical values set forth are indicated as precisely as possible. Any numerical value, however, may inherently contain certain errors or inaccuracies resulting, for example, from their respective measurement techniques, as evidenced by standard deviations associated therewith.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed in accordance with 35 U.S.C. §112, ¶6 unless the term "means" is expressly used in association therewith.

I claim:

1. A band electrode array comprising:
   a substrate;
   a first insulating layer disposed on the substrate;
   a first band electrode disposed on the first insulating layer;
      wherein the first band electrode has a thickness of about 1 nm-about 5000 nm and an exposed cross-sectional surface having a width of about 1 μm-about 1 cm;
   a second insulating layer disposed on the first insulating layer and completely covering the first band electrode; wherein the second insulating layer has a thickness of about 100 nm-about 500 μm;
   a second band electrode disposed on the second insulating layer; wherein the thickness of the second band electrode is about 1 nm-about 5000 nm and width of the exposed cross-sectional surface of the second band electrode is about 1 μm-about 1 cm;
   a third insulating layer is disposed on the second insulating layer and completely covering the second band electrode;
   wherein the first and second band electrodes are electrically insulated from each other and individually addressable; cross-sectional surfaces of the first and second band electrodes are exposed on the test surface and coextensive with the test surface; and the exposed cross-sectional surfaces substantially overlap each other in a direction perpendicular to the substrate.

2. The band electrode array of claim 1, wherein diffusion layers of the first and second band electrodes overlap.

3. The band electrode array of claim 1, further comprising a third band electrode disposed on the first insulating layer and completely covered by the second insulating layer, wherein the first, second and third band electrodes are electrically insulated from each other and individually addressable.

4. The band electrode array of claim 3, further comprising a fourth band electrode disposed on the second insulating layer and completely covered by the third insulating layer, wherein the first, second, third and fourth band electrodes are electrically insulated from each other and individually addressable.

5. The band electrode array of claim 1, wherein the first band electrode and/or the second band electrode are formed from a plurality of layers.

6. The band electrode array of claim 1, wherein at least one of the substrate, band electrodes, and insulating layers have a curvilinear or rectilinear form.

7. The band electrode array of claim 1, wherein the substrate is made of silicon, glass, plastic, rubber, silicone and/or a combination thereof.

8. The band electrode array of claim 1, wherein the first, second and third insulating layers are made of epoxy, silicone, polymer, oxide, nitride, carbide, plastic, rubber and/or a combination thereof.

9. The band electrode array of claim 1, wherein the first and second band electrodes are made of gold, silver, copper, platinum, palladium, carbon, conductive polymer, metal alloy, and/or a combination or mixture thereof.

10. The band electrode array of claim 1, wherein the exposed cross-sectional surface of the first band electrode is functionalized by a first chemical species and/or the exposed cross-sectional surface of the second band electrode is functionalized by a second chemical species, and the first and second chemical species are the same or different species.

11. A method of manufacturing the band electrode array of claim 1, comprising:
   (a) depositing the first insulating layer onto the substrate,
   (b) placing a first shadow mask on the first insulating layer,
   (c) forming the first band electrode in an opening of the first shadow mask by depositing a conductive film over the first shadow mask,
   (d) removing the first shadow mask,
   (e) depositing the second insulating layer such that the first band electrode is completely covered by the second insulating layer,
   (f) placing a second shadow mask on the second insulating layer,
   (g) forming the second band electrode in an opening of the second shadow mask by depositing a conductive film over the second shadow mask,
   (h) removing the second shadow mask,
   (i) depositing the third insulating layer such that the second band electrode is completely covered by the third insulating layer, and
   (j) cleaving or cutting a side surface of the band electrode array to form the test surface such that cross-sectional surfaces of the first and second band electrodes are exposed thereon and substantially overlap each other in a direction perpendicular to the substrate.

12. The method of claim 11, further comprising electrically connecting a first lead to the first band electrode between steps (d) and (e), and electrically connecting a second lead to the second band electrode between steps (h) and (i).

13. The method of claim 11, wherein the method does not comprise using photolithography or using e-beam lithography.

14. The method of claim 11, further comprising functionalizing the exposed cross-sectional surface of the first band electrode and/or the exposed cross-sectional surface of the second band electrode.

15. The method of claim 11, further comprising:
immersing the test surface of the band electrode array, a reference electrode and a counter electrode in an electrolyte;
applying a voltage on one of the band electrodes relative to the reference electrode such that a desired electrochemical reaction is induced on the exposed cross-sectional surface of the one band electrode and a desired chemical species is deposited thereon;
optionally applying another voltage at the same time to the other band electrode relative to the reference electrode such that no electrical current flows through the other band electrode.

16. The method of claim 14, wherein the desired chemical species is alkane thiols with different end groups, aromatic diazonium ions with different end groups, aromatic amines with different end groups, aliphatic or aromatic alcohols with different end groups, aliphatic and/or aromatic carboxylic compounds with different end groups, dihydroxy bezaldehydes with different end groups or a combination thereof.

17. A method of using the band electrode array of claim 1, comprising:
immersing the test surface of the band electrode array, a reference electrode and a counter electrode in an analyte solution;
applying a first voltage signal to the first band electrode such that a first electrochemical reaction is induced on the exposed cross-sectional surface of the first band electrode and a reaction product is generated in the vicinity thereof;
applying a second voltage signal to the second band electrode such that the reaction product undergoes a second electrochemical reaction on the exposed cross-sectional surface of the second band electrode and a resultant electrical current flows through the second band electrode; and
detecting and analyzing the electrical current through the second band electrode to determine characteristics of the first electrochemical reaction and properties of the reaction product.

18. The method of claim 17, further comprising:
terminating the second voltage signal as applied to the second band electrode; and
applying the second voltage signal to a third band electrode such that the reaction product undergoes an electrochemical reaction on the exposed cross-sectional surface of the third band electrode and the resultant electrical current flows through the third band electrode.

19. The method of claim 17, wherein the first voltage signal and/or the second voltage signal are constant DC voltages or voltages changing with time.

20. The method of claim 17, wherein the voltages changing with time are triangular voltage signals, sawtooth voltage signals, staircase signals, and/or a combination thereof.

21. The band electrode array of claim 1, wherein the thickness of the first band electrode is different than the thickness of the second band electrode.

22. The band electrode array of claim 1, wherein the width of the exposed cross-sectional surface of first band electrode is different than the width of the exposed cross-sectional surface of the second band electrode.

23. The band electrode array of claim 1, wherein the thickness of the first band electrode is different than the thickness of the second band electrode, and the width of the exposed cross-sectional surface of the first band electrode is different than the width of the exposed cross-sectional surface of the second band electrode.

* * * * *